(12) United States Patent
Lauer

(10) Patent No.: US 11,497,839 B2
(45) Date of Patent: Nov. 15, 2022

(54) CONTACT PROTECTION APPARATUS FOR A MEDICAL FLUID-CONDUCTING CASSETTE AND CASSETTE

(71) Applicant: Fresenius Medical Care Deutschland GmbH, Bad Homburg (DE)

(72) Inventor: Martin Lauer, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 557 days.

(21) Appl. No.: 16/481,378

(22) PCT Filed: Jan. 25, 2018

(86) PCT No.: PCT/EP2018/051855
§ 371 (c)(1),
(2) Date: Jul. 26, 2019

(87) PCT Pub. No.: WO2018/138208
PCT Pub. Date: Aug. 2, 2018

(65) Prior Publication Data
US 2020/0000991 A1    Jan. 2, 2020

(30) Foreign Application Priority Data

Jan. 30, 2017  (DE) .......................... 102017101730.5

(51) Int. Cl.
*A61M 1/16*      (2006.01)
*A61M 1/14*      (2006.01)
(Continued)

(52) U.S. Cl.
CPC ............ *A61M 1/1621* (2014.02); *A61M 1/14* (2013.01); *A61M 1/15* (2022.05); *A61M 1/156* (2022.05);
(Continued)

(58) Field of Classification Search
CPC .... A61M 1/14; A61M 1/1621; A61M 1/1686; A61M 1/267; A61M 1/287; A61M 1/367;
(Continued)

(56) References Cited

U.S. PATENT DOCUMENTS

| 5,441,636 A | 8/1995 | Chevallet et al. |
| 5,928,177 A | 7/1999 | Brugger et al. |

(Continued)

FOREIGN PATENT DOCUMENTS

| CN | 1658916 A | 8/2005 |
| CN | 101102936 A | 1/2008 |

(Continued)

OTHER PUBLICATIONS

International Preliminary Report on Patentability in Application No. PCT/EP2018/051855, dated Jul. 30, 2019, 6 pages (English Translation).

(Continued)

*Primary Examiner* — John Kim
(74) *Attorney, Agent, or Firm* — Fish & Richardson P.C.

(57) ABSTRACT

The present disclosure relates to a contact protection apparatus for covering connection point(s) of a medical fluid-conducting cassette used for a medical treatment. The contact protection apparatus includes at least one covering section for covering the connection point before the use of the cassette, and at least one connection section for detachably connecting the contact protection apparatus or for holding the contact protection apparatus on the cassette. It further relates to a medical fluid-conducting cassette with a contact protection apparatus.

30 Claims, 11 Drawing Sheets

(51) Int. Cl.
  *A61M 39/10* (2006.01)
  *F04B 43/00* (2006.01)
  *A61M 1/36* (2006.01)
  *A61M 39/18* (2006.01)
  *A61M 1/26* (2006.01)

(52) U.S. Cl.
  CPC .......... *A61M 1/367* (2013.01); *A61M 1/3622* (2022.05); *A61M 39/105* (2013.01); *A61M 39/18* (2013.01); *F04B 43/009* (2013.01); *A61M 1/267* (2014.02); *A61M 2205/12* (2013.01); *A61M 2205/6045* (2013.01)

(58) Field of Classification Search
  CPC .... A61M 39/18; A61M 39/20; A61M 39/105; A61M 2205/12; A61M 2205/6045; A61M 2209/06; A61M 1/15; A61M 1/156; F04B 43/009
  See application file for complete search history.

(56) References Cited

U.S. PATENT DOCUMENTS

| | | | |
|---|---|---|---|
| 6,234,538 | B1 | 5/2001 | Lauer |
| 6,743,201 | B1 | 6/2004 | Doing et al. |
| 2005/0230292 | A1 | 10/2005 | Beden et al. |
| 2008/0093246 | A1 | 4/2008 | Duchamp et al. |
| 2010/0274168 | A1 | 10/2010 | Gronau et al. |
| 2011/0064608 | A1 | 3/2011 | Lee et al. |
| 2011/0098635 | A1 | 4/2011 | Helmore et al. |
| 2012/0245535 | A1 | 9/2012 | Jacobsson et al. |
| 2013/0030348 | A1 | 1/2013 | Lauer |
| 2013/0030404 | A1 | 1/2013 | Gerlach et al. |
| 2013/0245531 | A1 | 9/2013 | Brandl et al. |
| 2016/0121097 | A1 | 5/2016 | Steele |
| 2017/0080204 | A1 | 3/2017 | Lauer |

FOREIGN PATENT DOCUMENTS

| | | |
|---|---|---|
| CN | 102596115 A | 7/2012 |
| CN | 105641803 A | 6/2016 |
| CN | 106075716 A | 11/2016 |
| CN | 106132472 A | 11/2016 |
| DE | 19814695 | 10/1999 |
| DE | 19828650 | 12/1999 |
| DE | 102011108781 | 1/2013 |

OTHER PUBLICATIONS

International Search Report and Written Opinion in Application No. PCT/EP2018/051855, dated Apr. 19, 2018, 9 pages (English Translation).

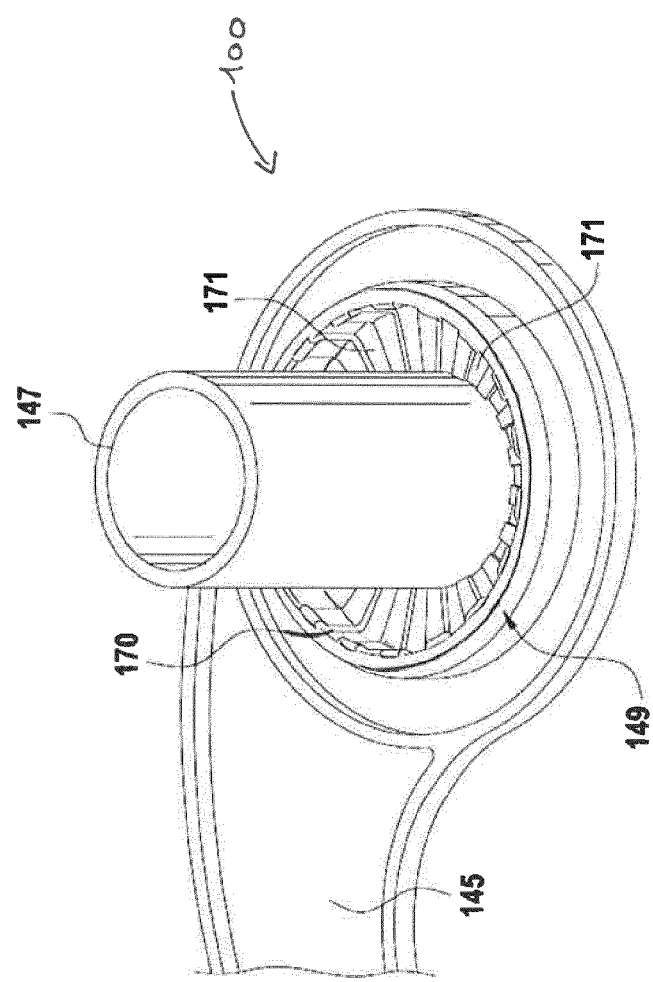

CONTACT PROTECTION APPARATUS FOR A MEDICAL FLUID-CONDUCTING CASSETTE AND CASSETTE

CROSS-REFERENCE TO RELATED APPLICATIONS

The present application is the national stage entry of International Patent Application No. PCT/EP2018/051855, filed on Jan. 25, 2018, and claims priority to Application No. DE 10 2017 101 730.5, filed in the Federal Republic of Germany on Jan. 30, 2017, the disclosure of which are expressly incorporated herein in entirety by reference thereto.

TECHNICAL FIELD

The present disclosure relates to a contact protection apparatus for covering a connection point of a fluid-conducting cassette for a medical fluid treatment. It further relates to a medical fluid-conducting cassette that is used for medical treatments.

BACKGROUND

Fluid-conducting cassettes are used in medical fluid treatment and are a separate component from the medical fluid treatment machine. The fluid-conducting cassettes are connected to the medical fluid treatment machine prior to medical fluid treatment. The fluid conducting cassette includes connection points that are used for adding a fluid into the cassette during the treatment of the patient (in short: fluid addition/connection points of the cassette). Various solutions are known from practice for preventing contamination of cassette connection points including, for example, using detachably adhered or strippable protective foils.

SUMMARY

The contact protection apparatus for covering a joint or connection point of a medical fluid-conducting cassette for a medical fluid treatment comprises at least one covering section for covering the connection point before the use of the cassette, i.e. before the cassette is mounted to a fluid treatment apparatus. It further comprises at least a first connection section for the detachable connection or holding of the contact protection apparatus to or on or at the cassette.

The at least one covering section of the contact protection apparatus is placeable on or over at least one connection point of a fluid-conducting cassette and preferably wide enough to cover this or several connection points of the cassette such that with normal use of the attached contact protection apparatus no area of the connection point can be contaminated by being touched with the fingers. The covering section may have any form known from the state of the art, for example it may be plate-shaped. It may be designed to be rectangular, semi-circular or the like, and so on. The size of the covering section may be chosen depending on the size of the individual connection point to be protected.

The contact protection apparatus comprises an upper side and a bottom side.

The present disclosure further relates to a medical fluid-conducting cassette with at least one contact protection apparatus.

In all of the following embodiments, the use of the expression "may be" or "may have" and so on, is to be understood synonymously with "preferably is" or "preferably has", respectively, and so on, and is intended to illustrate exemplary embodiments.

Embodiments may have one or more of the features mentioned supra or in the following. The features mentioned herein may in any combination be the subject-matter of the embodiments, provided that the person skilled in the art does not recognize a concrete combination as technically impossible.

Embodiments are also subject-matter of the independent claims and embodiments.

Whenever numerical words are mentioned herein, the person skilled in the art shall recognize or understand them as indications of numerical lower limits. Unless it leads the person skilled in the art to an evident contradiction, the person skilled in the art shall comprehend the specification for example of "one" encompassing "at least one". This understanding is also equally encompassed by the present invention as the interpretation that a numeric word, for example, "one" may alternatively mean "exactly one", wherever this is evidently technically possible for the person skilled in the art. Both are encompassed by the present invention and apply herein to all used numerical words.

Spatial information "top" or "bottom" are herein to be understood in case of doubt by the person skilled in the art as absolute or relative spatial information, which refer to the orientation of the respective component during normal use of the component.

During use, the upper side of the contact protection apparatus, in case of doubt, faces away from the hard part of the cassette; the bottom side faces said hard part.

In certain embodiments, the first connection section is an insert or plug-in connection or part thereof.

In certain embodiments, the covering section comprises at least a first structure—preferably projecting or extending from the bottom side of the contact protection apparatus—which is closed in its circumference.

In certain embodiments, the covering section comprises at least a second structure—preferably projecting or extending from the bottom side of the contact protection apparatus—which is closed in its circumference.

In certain embodiments, the contact protection apparatus comprises at least one grip section. The grip section preferably comprises at least one structure—in particular projecting or extending from the bottom side of the contact protection apparatus—which is preferably closed in its circumference.

In certain embodiments, the structure of the grip section, which optionally may also extend to the second connecting section, comprises at least one recess in its outermost edge.

A recess as used herein may be a section in which the structure comprising the recess is shorter than adjacent, optionally than both adjacent, sections of the structure. A recess may be a notch, a slot, or a cut. A recess is preferably not a closed through-opening. A recess may be designed similarly to a loophole.

In certain embodiments, the contact protection apparatus comprises at least one spacer, which is preferably adjacent to the grip section. The spacer preferably protrudes from the contact protection apparatus, preferably in a direction of the depth of the cassette, preferably from the bottom side of the contact protection apparatus. The spacer thus ensures a minimum distance, under which some sections of the contact protection apparatus, and in particular the grip section of the contact protection apparatus, on the one hand, and the hard part of the cassette, on the other hand, cannot come closer.

In this way, the spacer allows the user to grip between his fingers the grip section on both sides, i.e., on the upper side as well as on the bottom side thereof, in order to remove the contact protection apparatus.

In certain embodiments, the grip section optionally extends forward (i.e. in a direction of the main extension of the cassette) over or across the edge of the cassette or a hard part of the cassette. This may facilitate removing the contact protection apparatus for the user.

In certain embodiments, the contact protection apparatus, comprises at least a second connection section for releasably connecting the contact protection apparatus to the cassette or for holding or retaining the contact protection apparatus onto the cassette.

In certain embodiment, the second connection section comprises a projection, which is dimensioned and arranged to be inserted into a centering opening or retaining opening of the fluid-conducting cassette.

In some exemplary embodiments, the projection comprises one or more protrusions on the outside. These may promote a snap-in effect when the projection is locked in the centering or retaining opening.

In certain embodiments, the second connection section comprises a structure—projecting or extending in particular from the bottom side of the contact protection apparatus—which is preferably closed in its circumference.

In certain embodiments, the structure comprises at least one recess in its outermost edge.

In some exemplary embodiments, the second connection section comprises optionally at least a first through-opening and/or a second through-opening.

In certain embodiments, the grip section is arranged between the first connection section and the second connection section or it connects both.

In certain embodiments, the contact protection apparatus comprises at least a first through-opening in the area of the second connection section. The through-openings connect, for example, the upper side of the contact protection apparatus to a bottom side of the contact protection apparatus.

In certain embodiment, the contact protection apparatus comprises at least one spacer in the area of the first connection section.

The spacer, for example, extends adjacently to the connection section and in the same spatial direction as the latter.

The covering section is in some embodiments held on the cassette in particular exclusively by means of tension or material stiffness. In these embodiments, there is no firmly bonded connection or adhesive joint between the covering section and the cassette.

In some embodiments the contact protection apparatus is embodied and/or connected to be removable from the cassette without being damaged. The contact protection apparatus is in some embodiments held on the cassette by a first connection section. The connection section provides for a detachable and stable connection of the contact protection apparatus with the cassette. This connection may be done without adhesives. It may be a latching, arresting or locking, insertion, clamping, screwing, holding by physical force, or another type of detachable connection known from the state of the art.

In some embodiments the contact protection apparatus is embodied to be repeatedly connectable with and detachable from the cassette.

In certain embodiments, the contact protection apparatus is plate-shaped. In some embodiments, the contact protection apparatus is one-piece or integral. However, it is recognizable for the person skilled in the art that the contact protection apparatus may both have any arbitrary form known from the state of the art in order to function and be produced to be or have one or more pieces or parts.

In some embodiments, the contact protection apparatus is held on the cassette only by the first and if necessary by a second connection section.

In some embodiments, the contact protection apparatus comprises at least one encoding structure for an arrangement which is encoded on the fluid-conducting cassette in relation to the shape of the contact protection apparatus. The encoded arrangement may contribute to a stable connection of the contact protection apparatus with the cassette. For this, the encoding structure has a shape which for example correlates or complements or is complementary with the shape or contour of an edge (or a different area) of the cassette. This effects on the one hand a stable connection between the contact protection apparatus and the cassette which in an edge area of the cassette proceeds to the shape of the encoding structure in a complementary manner. Thus, the encoding structure may prevent for example shifting of the contact protection apparatus or twisting around the axis of the connection with the cassette, for example around the connection section. On the other hand, the encoding structure may advantageously prevent mounting of the contact protection apparatus to the cassette in a position other than intended during the production process. Thus, a mounting of the contact protection apparatus which is ineffective for the intended contact protection may advantageously be prevented.

In some embodiments, the encoding structure of the contact protection apparatus is undulating or comprises an undulating section. It is recognizable for the person skilled in the art that the encoding structure may have any conceivable form by means of which it can fulfill at least one of the above-mentioned functions or advantages. For example, it may comprise a straight line, a zigzag pattern or any other stepped pattern. It may comprise a continuous or a non-continuous pattern, and so on.

In certain embodiments, the encoding structure of the contact protection apparatus is a recess provided for this purpose in at least one section or on one side of the contact protection apparatus.

In some embodiments, the contact protection apparatus comprises at least one fixing device for the detachable intake, delimitation or fixation of inlet and/or outlet tubes of the fluid-conducting cassette.

For this, the fixing device holds the tubes in some embodiments in a desired position relative to the cassette. The fixing device may thus prevent the tubes from being damaged by kinking or prevent contamination by unintended detachment of the tubes from the cassette.

In certain embodiments, the fixing device is designed to be multi-part. Between the individual sections of the multi-part fixing device, other objects such as for example tube clamps which in turn may be connected with the above-mentioned tubes may be held temporarily by means of friction or latching effect. This may serve the protection of the objects at least until the use of the cassette.

In some embodiments of the contact protection apparatus, the fixing device is arranged only on one side of the contact protection apparatus. It extends only on one side.

In some embodiments, the contact protection apparatus comprises a substantially planar, completely planar or exclusively planar surface. This surface faces away from the connection point during use of the contact protection apparatus. The planar surface advantageously prevents an unintended entangling of the contact protection apparatus with other objects before the use of the cassette or getting caught on these which could detach the contact protection apparatus unintentionally from the cassette.

In certain embodiments, the contact protection apparatus comprises at least one grip area for grasping the protection apparatus in order to detach the contact protection apparatus from the fluid-conducting cassette by hand. Using the grip section, the user removes or detaches the contact protection apparatus from the cassette, e.g., before inserting the cassette into a fluid treatment apparatus.

The grip section may have any design known from the state of the art, in particular such which facilitates or enables a non-slip holding or grasping of the grip area. For example, the grip area may be designed as a ring, studs or knobs, latch and so on or comprise a fluting or riffles or a rough surface.

In some embodiments of the contact protection apparatus, the covering section is not present on the grip section, but on a different section of the contact protection apparatus. This has the effect that the covering section does not have to be touched in order to detach the contact protection apparatus from the cassette. It thus minimizes the risk of unintended contamination during detachment of the contact protection apparatus.

In certain embodiments of the contact protection apparatus, the grip section is present on a section of the contact protection apparatus which is opposite the covering section. This may contribute to a detachment of the contact protection apparatus from the cassette without contamination.

In some embodiments of the medical fluid-conducting cassette, the contact protection apparatus is connected with the cassette without adhesives.

In some embodiments, the contact protection apparatus comprises a section which protrudes from the edge of the cassette.

In some embodiments, the grip section of the contact protection apparatus is arranged on the section which protrudes from the edge of the cassette, in order to facilitate the removal of the contact protection apparatus from the cassette for the user.

In certain embodiments of the contact protection apparatus, its second connection section is introduced in at least one retaining hole or a centering hole of the cassette in order to connect the contact protection apparatus—optionally supported by this measure—with the cassette. This retaining hole or centering hole of the cassette may be provided to be connected with a centering or retaining device of a fluid treatment apparatus. It serves to, for example, hold or center the cassette at the fluid treatment apparatus during use, for example during a dialysis treatment.

In some embodiments, the connection section of the contact protection apparatus during use prevents the cassette from being mounted to a fluid treatment apparatus or the cassette from being inserted herein. This is achieved for example in that when the contact protection apparatus is connected with the cassette, the connection section is stuck or plugged in the centering hole or retaining hole of the cassette. As the cassette with the attached contact protection apparatus cannot be mounted to the fluid treatment apparatus because its centering hole is not exposed, the contact protection apparatus has to be deliberately removed first.

In further embodiments, the contact protection apparatus is designed, for example by dimensions or type of connection with the cassette, such that the cassette with the attached contact protection apparatus may be mounted to the fluid treatment apparatus, however, e.g., a cover, or for example a machine door of the apparatus, cannot be closed without the contact protection apparatus having first been removed from the cassette. This also serves to ensure that the contact protection apparatus has been reliably removed before the use of the cassette.

In some advantageous embodiments, the contact protection apparatus is sterilized together with the cassette. The sterilization process of the cassette takes place with the attached contact protection apparatus in these embodiments. This is possible as in such embodiments there is no firmly bonded or steam-impermeable connection between the covering section of the contact protection apparatus—(located on the connection point) and the cassette and/or the connection point. Thus, e.g. the steam permeability of the contact protection apparatus is ensured. The connection point may be successfully sterilized even with the attached contact protection apparatus or covering section, for example with hot steam.

This advantage may also arise if or when the contact protection apparatus and the cassette are made of the same material or similar materials, at least of materials which can be sterilized by means of the same sterilization process which can be used to sterilize the cassette.

In some embodiments, the at least one connection point which is or will be covered by the covering section is a joint for a substituate line.

In a further embodiment, the medical fluid-conducting cassette is designed as a blood cassette, for example for the dialysis treatment, in particular for hemodialysis, hemofiltration, hemodiafiltration, peritoneal dialysis, acute dialysis, and so on.

In some advantageous embodiments, the depth of the centering opening of the fluid-conducting cassette is larger than the height of the projection of the second connection section.

In some advantageous embodiments, the cassette comprises in the area of the second connection section projections whose geometries are adapted to the shape of the first and/or second through-opening.

In some embodiments, the first structure of the contact protection apparatus or of the covering section, which is arranged like a concentric ring around the center of the covering section, forms, together with a tubular channel structure of the connection point of the cassette, a labyrinth seal by inserting two annular structures into each other.

In some exemplary embodiments, the body of the medical device, which is usually produced by an injection molding process and is therefore referred to herein as "hard", wherein said body may be covered with a comparatively soft film, and/or attachments like tubes etc. of said body, is to be understood as being the hard part (also referred to as hard body or substrate). The hard part may be made of PP (polypropylene), PE (polyethylene), PA ABS, PMMA, PC, PVC or other polymers or other materials known to the person skilled in the art. It may be made of insulator materials, such as, for example, ceramics.

In some exemplary embodiments, the first structure of the covering section, the second structure of the covering section, the circumferential structure of the second connection section and/or the circumferential structure of the grip area comprise one or several recesses, cuts or depressions.

In some exemplary embodiments, the fixing device is designed as a holder for the rinse port adapter, with the latter being inserted into the first.

In some exemplary embodiments, the fixing device comprises one, two or more joints, in particular film joints, with which the fixing device is connected to the hard part of the contact protection apparatus, e.g. to the second connection section.

In some exemplary embodiments, the fixing device has a cylindrical insert or plug-in section, which is surrounded by an annular structure. A gap is provided between the cylindrical insert section and the annular structure, in which gap the front end of the rinse port adapter may be held therein after or through being snapped in or if necessary jammed in.

In some exemplary embodiments, the fixing device comprises optionally three circular structures or surfaces.

In some advantageous embodiments, the contact protection apparatus comprises a drainage structure.

In some advantageous embodiments, the drainage structure comprises or consists of grooves extending for example, radially from the fixing device, here, for example, the insert section for receiving, for example, a rinse port adapter.

In some advantageous embodiments, the grooves extend at the bottom between the projected insert section and the annular structure surrounding the insert section.

Some or all embodiments may comprise one, several or all of the advantages named above and/or hereafter.

The contact protection apparatus may reduce the amount of force required to detach the contact protection apparatus from the cassette.

The contact protection apparatus may reduce risk of unintentionally contaminating the connection point of the cassette, for example by touching it with the hand, as the grip area of the contact protection apparatus is spaced far enough from the covering section.

Some contact protection apparatuses are made of the same material as the cassette and may undergo the same sterilization processes as the cassette. In addition, it may be disposed of the same way as or together with the cassette.

The contact protection apparatus and the cassette may be detached from each other using one hand.

The contact protection apparatus is made of soft or flexible materials or rounded edges such that a risk of injury for the user during its operation as well as the risk of damaging other parts of the contact protection apparatus or the cassette, for example by sharp contours, may be reduced.

The contact protection apparatus may reduce the potential for residual adhesive on the cassette when the contact protection apparatus is detached from the cassette, and may reduce the risk that the adhesive gets into the interior of the cassette via the connection point.

The contact protection apparatus may also reduce the risk of unintentionally touching the connection point when unpacking the cassette. In contrast to using some types of protective foils and sterilizing caps, the contact protection apparatus described herein may be attached to the cassette during the sterilization of the cassette. Accordingly, separate sterilization of the contact protection apparatus and the cassette, with subsequent assembly, is advantageously not necessary.

BRIEF DESCRIPTION OF THE FIGURES

The present disclosure is hereafter exemplarily explained by means of the appended drawings in which identical reference numerals refer to identical or similar components. In the figures, it applies that:

FIG. 12 shows a part of the contact protection apparatus in a perspective view and from the bottom side, in a fourth embodiment.

DETAILED DESCRIPTION OF THE FIGURES

Figure 1:
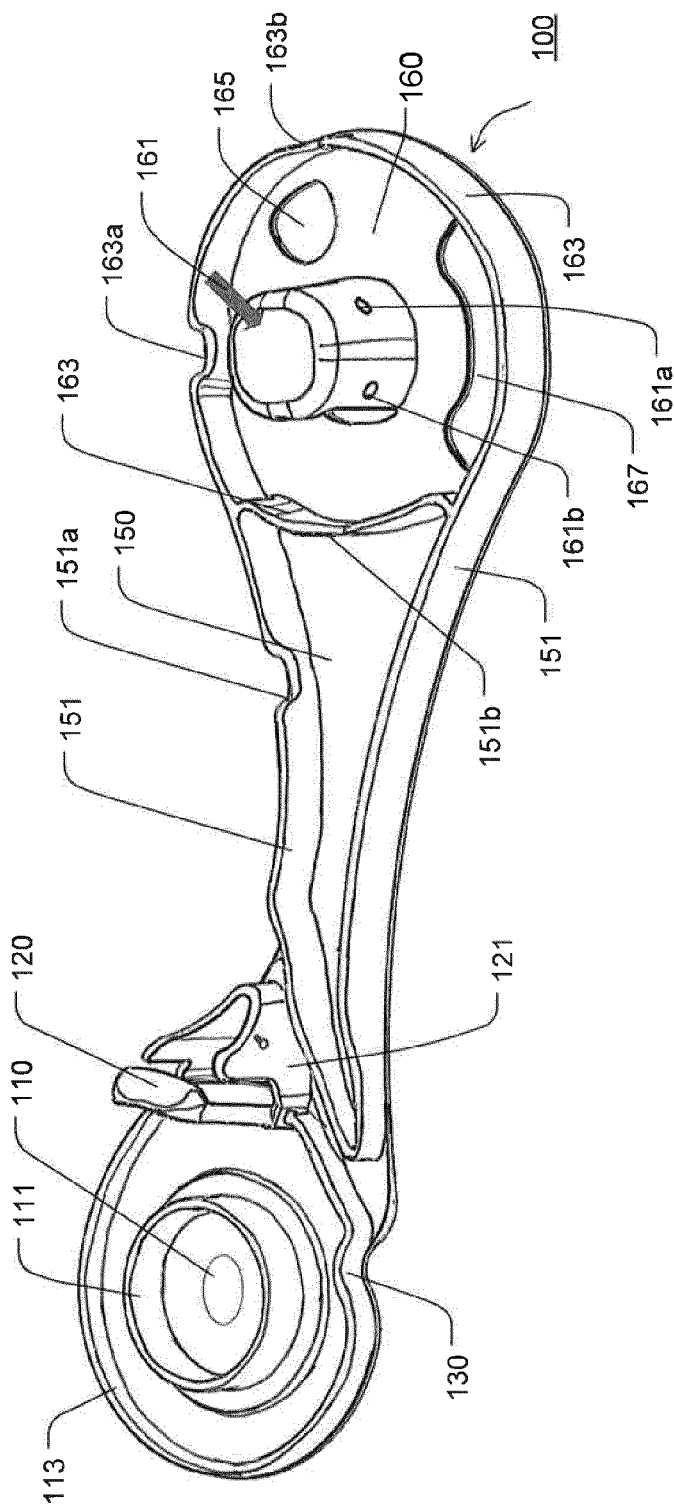
FIG. 1 shows a first embodiment of the contact protection apparatus obliquely from below, with a view on a bottom side which during use faces the fluid-conducting cassette.
Figure 2:
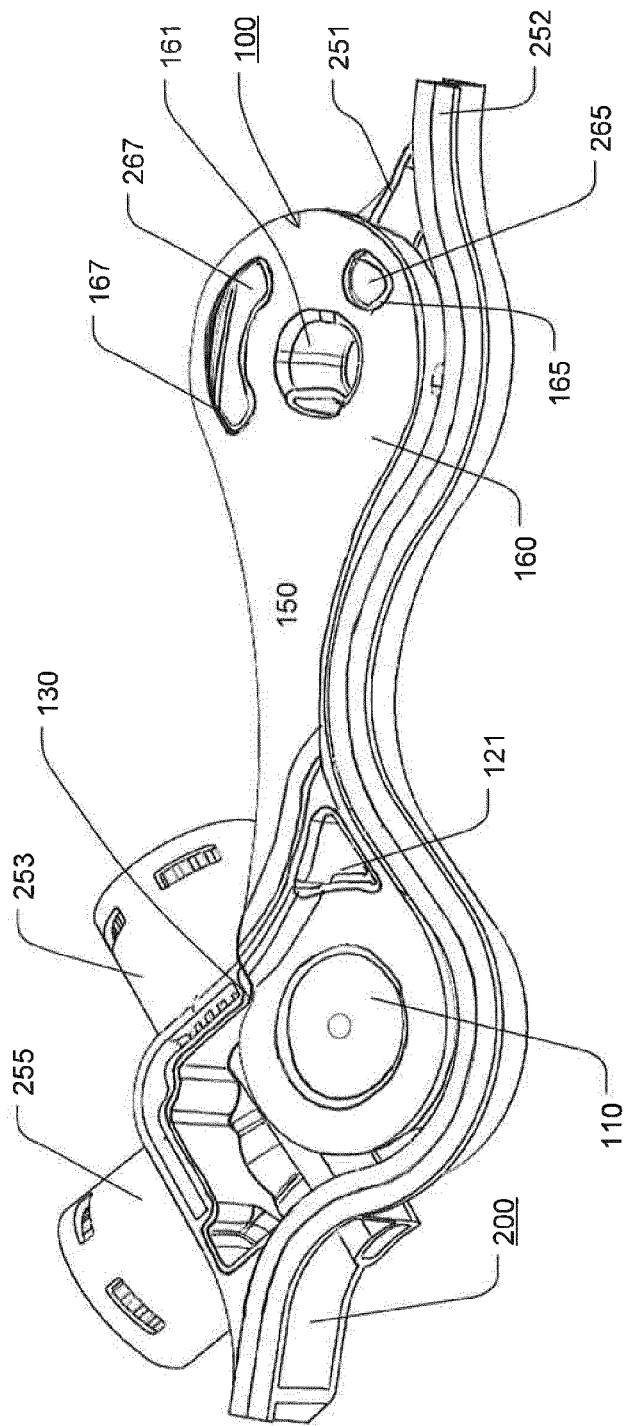
FIG. 2 shows obliquely from the top, the contact protection apparatus of FIG. 1 (i.e. with a view on the upper side)

FIG. 1 shows a first embodiment of the contact protection apparatus 100. The contact protection apparatus 100 comprises a covering section 110, a connection section 120, an optional encoding structure 130 and a grip section 150. The contact protection apparatus 100 comprises a first side (upper side, as shown in FIG. 2) and a second side (bottom side, as shown here in FIG. 1). The first side is opposite the second side.

Figure 3:
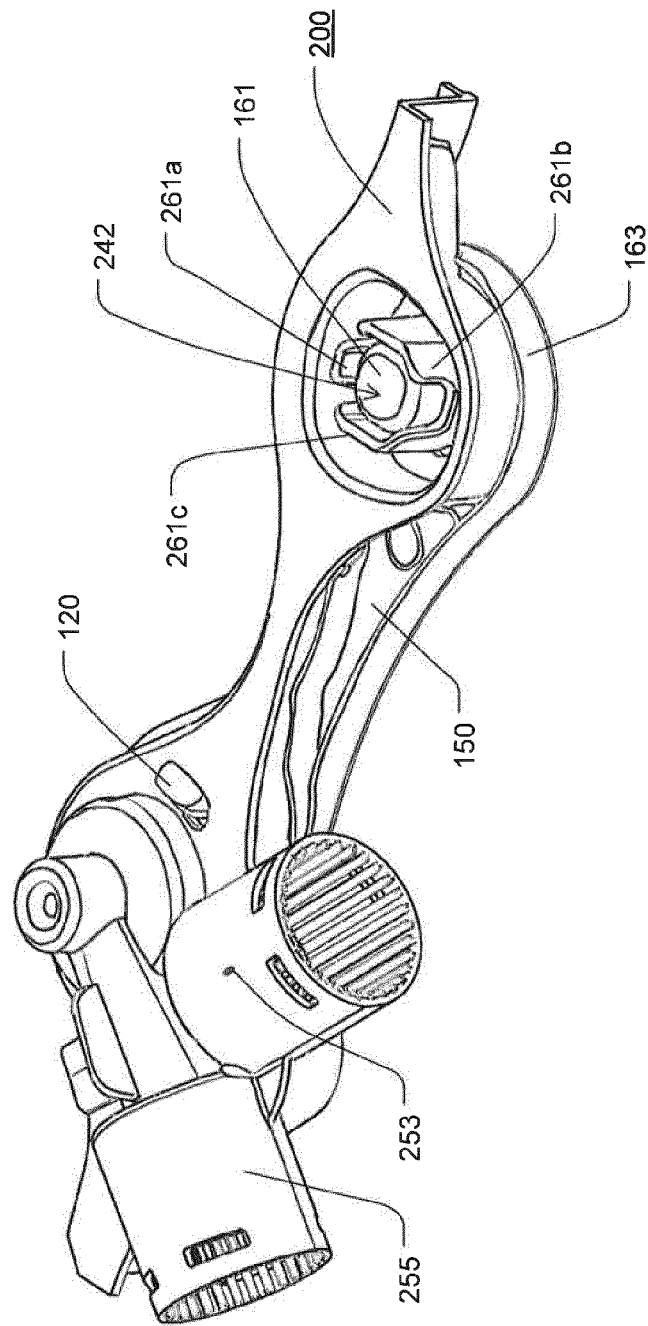
FIG. 3 shows the contact protection apparatus of FIGS. 1 and 2 from below, being connected to the cassette which is only illustrated in section.
Figure 4:
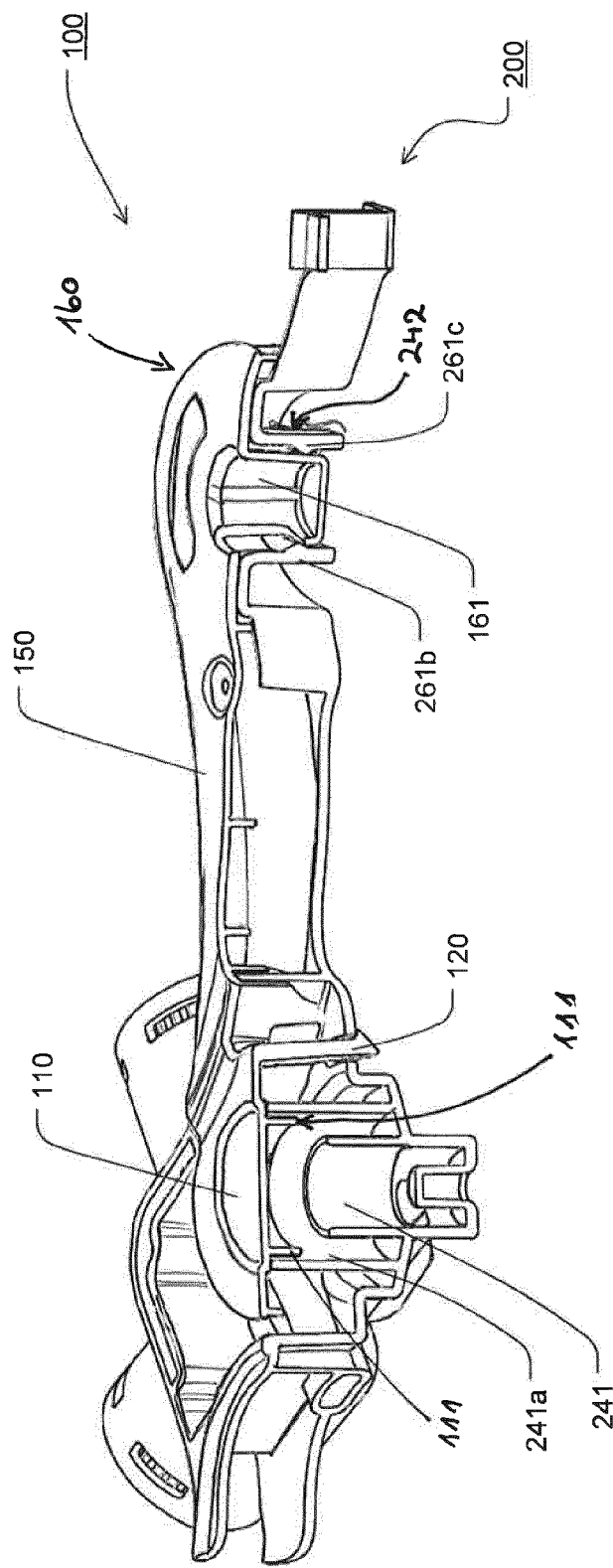
FIG. 4 shows in a perspective view similar to FIG. 2 the contact protection apparatus in a longitudinal section.

In this, the covering section 110 serves, in use, to cover a connection point 241, not shown in FIG. 1 (see FIG. 4). The covering section 110 is wide enough to completely cover the connection point 241 of a fluid-conducting cassette 200 (also not shown in FIG. 1, see however FIG. 2 to FIG. 6c), by means of which a fluid connection may be established to the cassette 200. Thus, an unintended touching by a user of the connection point 241 of the cassette 200 before use, i.e. before mounting the cassette 200 to a fluid treatment apparatus, is prevented by the covering section 110.

The covering section 110 is held on the cassette 200 by means of tension or via the material stiffness of the contact protection apparatus 100. The contact protection apparatus 100 in turn is held on the hard part of cassette 200 by means of, for example, and/or, inter alia, the connection section 120.

The connection section 120 provides for a detachable and stable connection of the contact protection apparatus 100 with the cassette 200. This connection is without adhesives and may be a latching, arresting or locking, insertion, clamping, screwing or another type of detachable connection known from the state of the art. The connection section 120 is in the example of FIG. 1 a plug-in connection or latching connection.

In some embodiments, the contact protection apparatus 100 is held on the cassette 200 only by the connection section 120. In others, as is also shown in the figures, a second connection section 160 is provided.

Between the covering section 110 and the cassette 60 there is in some embodiments no firmly bonded connection.

The contact protection apparatus 100 comprises a first structure 111 around the covering section 110. The latter is embodied as a closed structure, namely with a continuous circumference, i.e. a non-interrupted circumference.

An optional, second structure 113 surrounds the first structure 111 and, again, is optionally embodied as a closed structure.

While the first structure 111 preferably serves for a seal (as can be seen from FIGS. 4 to 6d), the second structure 113 preferably serves to reinforce the contact protection apparatus 100, and in particular the cover section 110.

Further, the second structure 113 may serve to center or align the contact protection apparatus 100 on the cassette 200, which in turn may help to ensure that the contact protection apparatus 100 is correctly placed on the cassette 200.

The first connection section 120 is here exemplarily designed as a latching section, which may engage and lock into a corresponding opening or through-opening (shown in FIG. 3) of the cassette 200.

Furthermore, the example of FIG. 1 shows an optionally provided spacer 121. It optionally ensures a desired spacing between the contact protection apparatus 100 and the cassette 200.

The shape of the spacer 121 is optionally angular or triangular in the cross section. The shape, in turn, serves to center or align the contact protection apparatus 100 on the cassette 200; it is adapted or corresponds to a geometrical particularity of the hard part of the cassette 200. In this specific embodiment, the spacer 121 may therefore also be understood as an encoding structure.

The grip section 150 comprises a structure 151, which, here, may optionally be embodied similar to the first and second structures 111 or 113 with a closed circumference.

The circumference of the structure 151 may also optionally be invariably raised, i.e. beyond or above the bottom area. This provides increased stiffness along the entire grip section 150, or even the entire contact protection apparatus 100, which may ensure a removal of the contact protection apparatus 100 from the cassette 200 without jamming or canting, no matter which point the user is acting on or touching to remove the contact protection apparatus 100 from the cassette 200 with his fingers being on the grip section 150.

The structure 151 may comprise one or more recesses, similar or identical to the herein exemplarily shown recesses 151a and/or 151b. Such recesses, on which the protruding edge of the structure 151 is lower than the recess of the adjacent section of the structure 151, may, in turn, serve to center or align the contact protection apparatus 100 on the cassette 200 through bars of the hard part of the cassette 200, see for example the bar 251 of FIG. 2.

In addition, recesses, such as the recesses 151a and/or 151b shown by way of example, may allow arranging the contact protection apparatus 100 at a level of an upper end of the hard part, approximately in the area of the circumferential structure 252, on which a film, not shown in the figures, is welded to the hard part. This makes it possible to advantageously keep small the thickness of the cassette 200 on which the contact protection apparatus 100 is placed.

In the exemplary embodiment of FIG. 1, the contact protection apparatus 100 also comprises at least the aforementioned second connection section 160. The second connection section 160, like the first connection section 120, may releasably connect the contact protection apparatus 100 with the cassette 200.

The second connection section 160 comprises a projection 161. It may be correspondingly shaped to be inserted into a centering opening 242 of the cassette 200 which is shown in FIG. 3. In this, the centering opening 242 may have an arbitrary number of latching noses 261a, 261b, 261c, which may serve the releasable connection between projection 161 and centering opening 242.

The projection 161 may comprise protrusions on the outside, such as the protrusions 161a, 161b, exemplarily shown herein, which may serve the latching.

The second connection section 160 may comprise a structure 163, which here may optionally be configured with a closed circumference similar to the a.m. first and second structures 111 or 113.

The structure 163 may also comprise one or more recesses 163a, 163b with the a.m. advantages and configurations.

Finally, FIG. 1 shows that the second connection section 160 optionally comprises at least a first through-opening 165 and a second through-opening 167. These may serve to receive projections 265, 267 (see FIG. 2) of the cassette 200. They may thus be used for centering and aligning as described above.

The encoding structure 130 contributes to a stable connection of the contact protection apparatus 100 with the cassette 200.

The encoding structure 130 comprises a shape that correlates with, or complements or is complementary to, the shape or contour of an edge or a section of the hard part of the cassette 200.

In the example of FIG. 1, all the structures are provided exclusively on the bottom of the contact protection apparatus.

FIG. 2 shows the contact protection apparatus 100 of FIG. 1 obliquely from above (i.e. with a view on an upper side).

In FIG. 2, the contact protection apparatus 100 is, according to the intended use, releasably mounted on the cassette 200, which is shown only in sections. Thereby, the covering section 110 covers the connection point 241 protectively.

The connectors 253 and 255 for connecting the optional substituate tube with the cassette 200 can be seen.

As can be seen in FIG. 2, the contact protection apparatus 100 comprises, in some embodiments, no raised structures at all on one side (here on the upper side), in any case no structures rising above a main longitudinal plane of the upper side.

FIG. 3 shows the contact protection apparatus 100 of FIGS. 1 and 2 from below, connected to the cassette 200 shown only in sections.

The first connection section 120 protrudes with an end section through one opening in the hard part of the cassette 200, wherein it latches with the hard part in the example of FIG. 3.

The user removes or releases the contact protection apparatus 100 from the cassette 200 by gripping the grip section 150 prior to inserting the cassette 200 into a fluid treatment apparatus.

It can be seen that the projection 161 is optionally releasably held in the centering opening 242 by (here optionally three) elastic noses 261a, 261b and 261c. The centering opening 242 is herein optionally surrounded and limited by the latching noses or noses 261a, 261b, 261c.

FIG. 4 shows in a perspective view, which is similar to that of FIG. 2, the contact protection apparatus 100 in a longitudinal section.

The first connection section 120 is latched with the hard part of the cassette 200 in FIG. 4 just like the second connection section 160 (see projection). The projection 161 is releasably held in a lower area by the elastic noses 261a, 261b and 261c. These have, optionally, ends which extend in a cross-section as latching protrusions (see FIG. 4) which inhibit the longitudinal movement of the protrusions or latching protrusions 161a, 161b.

As is further seen in FIG. 4, the depth of the centering opening 242, to which also the elastic noses 261a, 261b, and 261c may contribute, is greater than the height of the projection 161 of the second connection section 160. Therefore, the projection 161 does not project downward from the centering opening 242 (relative to the arrangement in FIG. 4). A benefit which can be achieved with the size relationship between the depth of the centering opening 242 and the height of the projections 161 may be that the contact protection apparatus 100 cannot be unintentionally removed by unintended pressure on the projection protruding from the centering opening 242 in another embodiment.

It can also be seen that the first structure 111, which is arranged like a concentric ring around the center of the covering section, forms together with a tubular channel structure 241a of the connection point 241 of the cassette 200, an (optionally simple) labyrinth seal, in which two tubular structures are inserted in each other.

Figure 5:
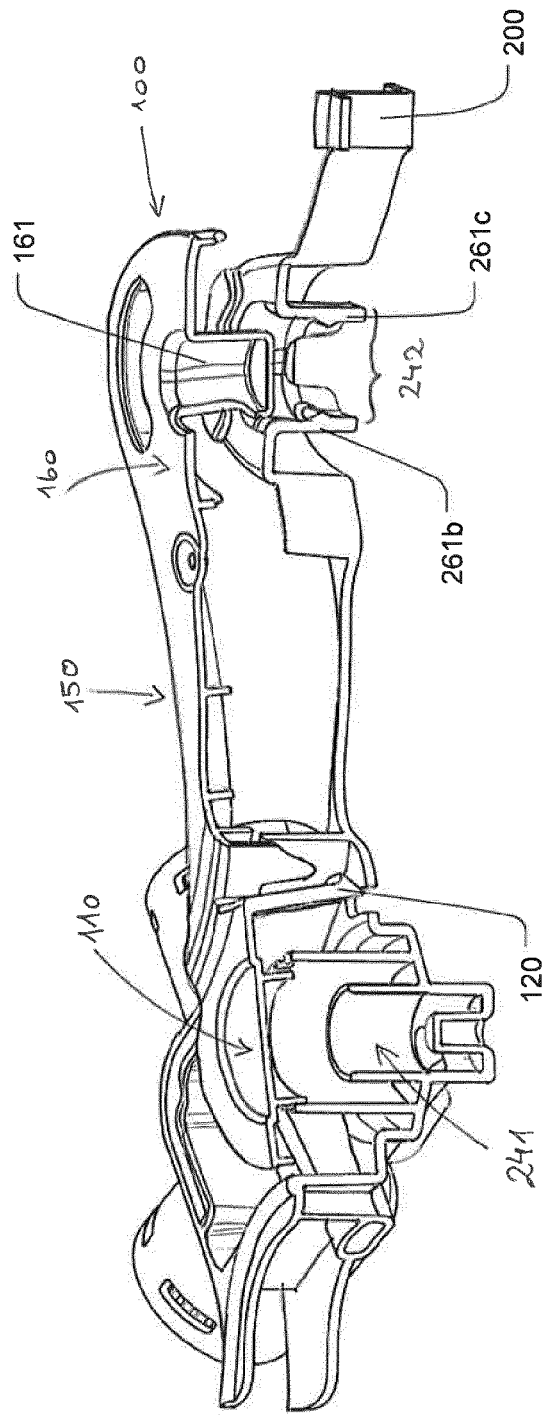
FIG. 5 shows a perspective view of the contact protection apparatus of the preceding figures, in use on a fluid-conducting cassette.

FIG. 5 shows the contact protection apparatus 100 in the illustration of FIG. 4, not connected to the hard part of the cassette any longer. The latching with the hard part, which is still present in FIG. 4, is clearly released in FIG. 5. This relates to both the first connection section 120 and also the optional, second connection section 160. Thus, the labyrinth seal of the first connection section 120 is about to be released. The bottom-side section of the projection 161 is already guided past the latching projection of the elastic noses 261a, 261b and 261c upwards.

When or if the contact protection apparatus 100 is connected to the cassette 200, as is shown in FIG. 4, the second connection section 160 plugs into the centering opening 242 or retaining opening of the cassette 200 provided for centering or retaining the cassette in a fluid treatment apparatus. The cassette 200 cannot be mounted to the fluid treatment apparatus in this state as the centering opening 242 is not freely accessible. As, however, a free access to the centering opening 242 is a prerequisite for mounting the cassette 200 to the fluid treatment apparatus, the contact protection apparatus 100 has to be deliberately removed The contact protection apparatus 100 may also be designed, for example through its dimensions or its type of connection with the cassette 200, such that the cassette 200 with attached contact protection apparatus 100 may be mounted to the fluid treatment apparatus, however, e.g., the door of the apparatus may not be closed before the contact protection apparatus 100 is detached from the cassette 200. This also serves to ensure that the contact protection apparatus 100 is or was reliably removed before the use of the cassette 200.

Detaching the contact protection apparatus 100 takes place without considerable application of force. It further takes place with a reduced risk of unintentional contamination of the connection point 241 of the cassette 200, for example by touching it with the hand, as the grip section 150 of the contact protection apparatus 100 is spaced from the covering section 110.

Not least because of the spacer 121, the grip section 150 protrudes beyond the hard part of the cassette 200 or is spaced from the hard part in a direction of the depth of the cassette 200 (i.e. in a direction in which the projection 161 extends longitudinally). This allows the user to grip the grip section 150 on both sides, thus to grip the upper side as well as the bottom side thereof between the fingers to remove the contact protection apparatus 100.

Further, the grip section 150 optionally projects forwardly (i.e. in a direction of the main extension of the cassette 200) over or beyond the edge of the cassette 200. This also facilitates the removal of the contact protection apparatus 100 for the user.

Figure 6C:
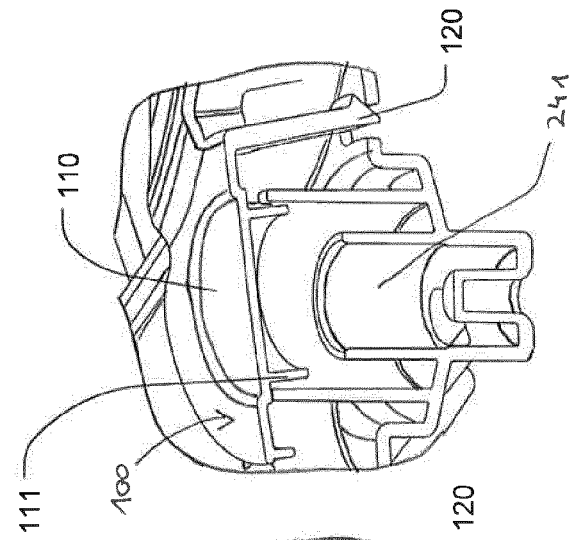
FIG. 6a-6c show the first connection section of the contact protection apparatus of the first embodiment in three stages of the transition from the engaged or locked state (FIG. 6a) to the disengaged or unlocked state (FIG. 6c)
Figure 6B:
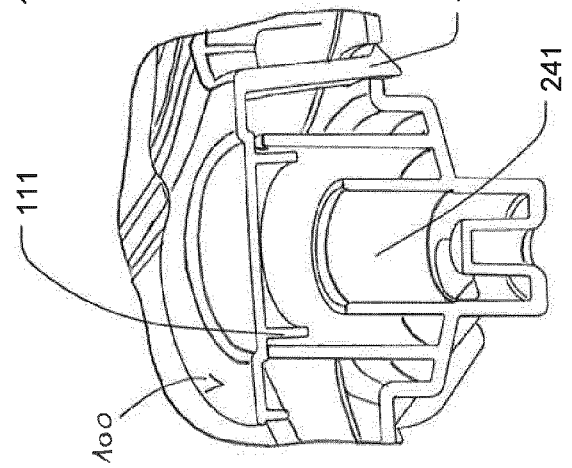
Figure 6A:
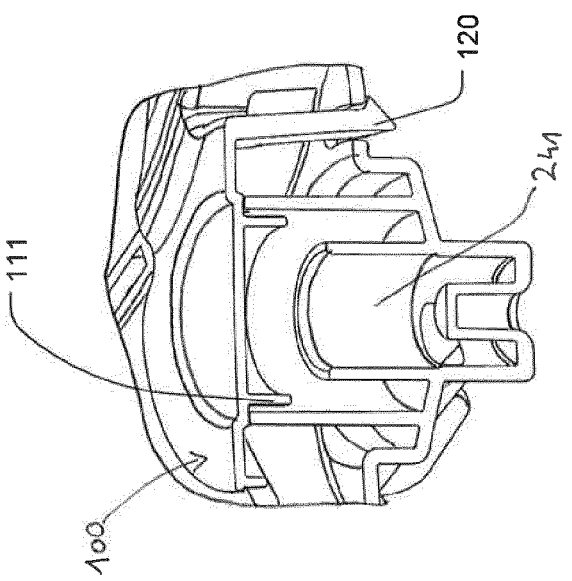

FIGS. 6a to 6c show the first connection section 120 of the contact protection apparatus 100 of the first embodiment in three stages of the transition from the latched or locked state (FIG. 6a) to the unlatched state (FIG. 6c).

It can be seen from the sequence of FIGS. 6a to 6c that the connection section 120, configured as a latching arm, is latched in the connected state under bending pre-stressing. This may advantageously allow to compensate for a distance tolerance between the connection point 241 and the centering opening 242 or retaining opening.

It can also be seen in FIG. 6c that the labyrinth seal made of or with the first structure 111 and the tubular channel structure 241a is intended or provided with a sufficient radial distance between the first structure 111 and the tubular channel structure 241a, in order to compensate for a tolerance in the distance between the connection point 241 and the centering opening 242 or retaining opening.

Figure 7:
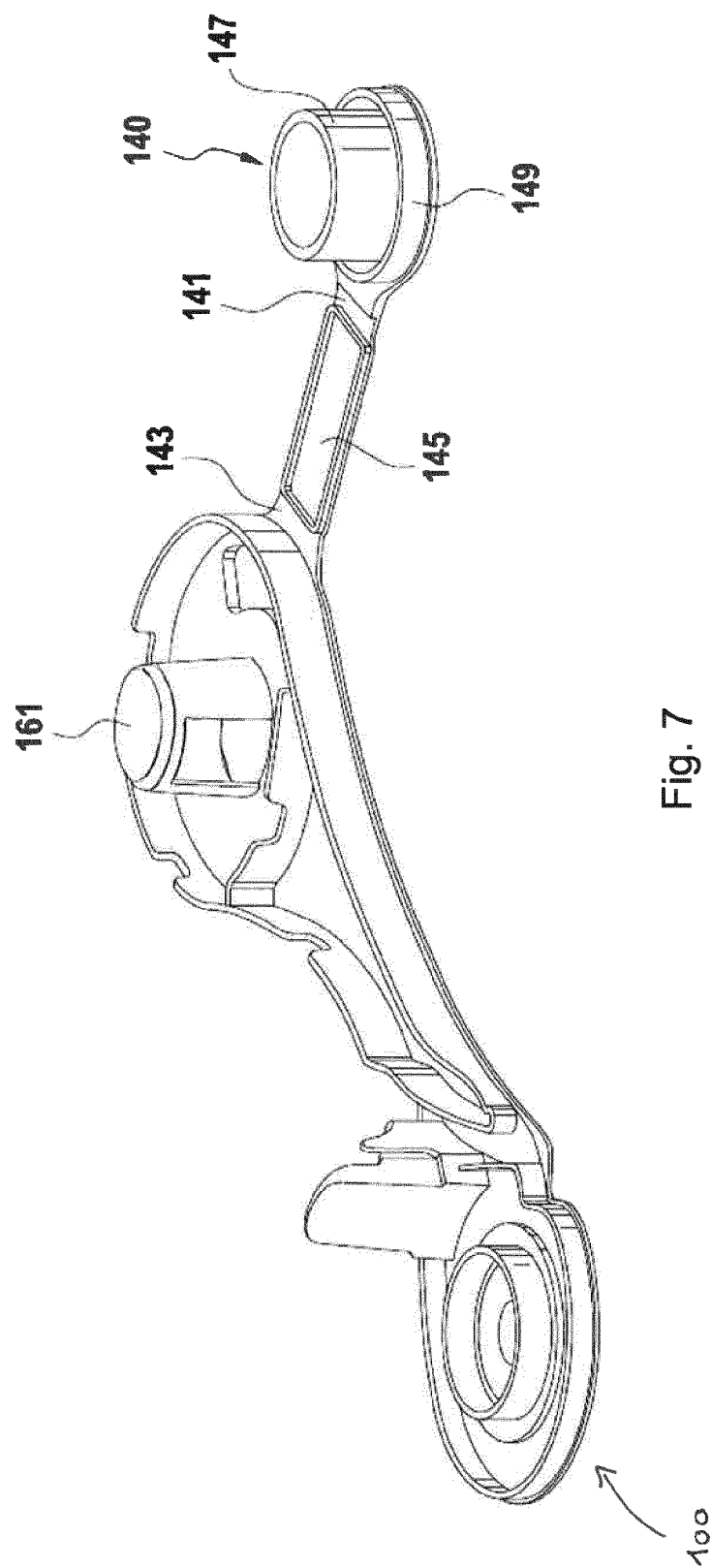
FIG. 7 shows the contact protection apparatus in a second embodiment.

FIG. 7 shows the contact protection apparatus 100 in a second embodiment with a holding or fixing device 140. Apart from the fixing device 140, the contact protection apparatus 100 of FIG. 7 is not different from that of the preceding figures.

The fixing device 140 is optionally provided. It serves, if present, for the direct or indirect releasable reception of e.g. inlet and outlet tubes. The fixing device 140 holds such tubes in a desired position relative to the cassette 200. It can thus prevent damage to the tubes by kinking, as well as their contamination by unintentionally detaching the tubes from the cassette 200.

Figure 8:
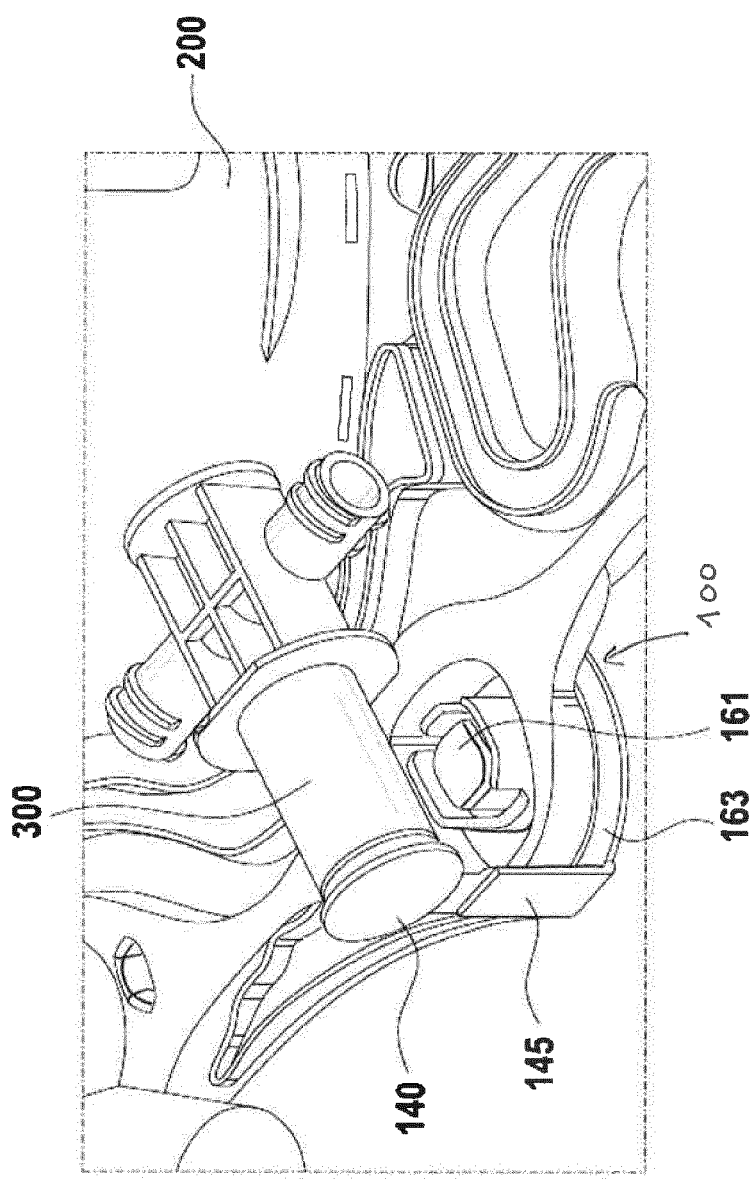
FIG. 8 shows the contact protection apparatus of FIG. 7 with a rinse port adapter attached on the fixing device.
Figure 11:
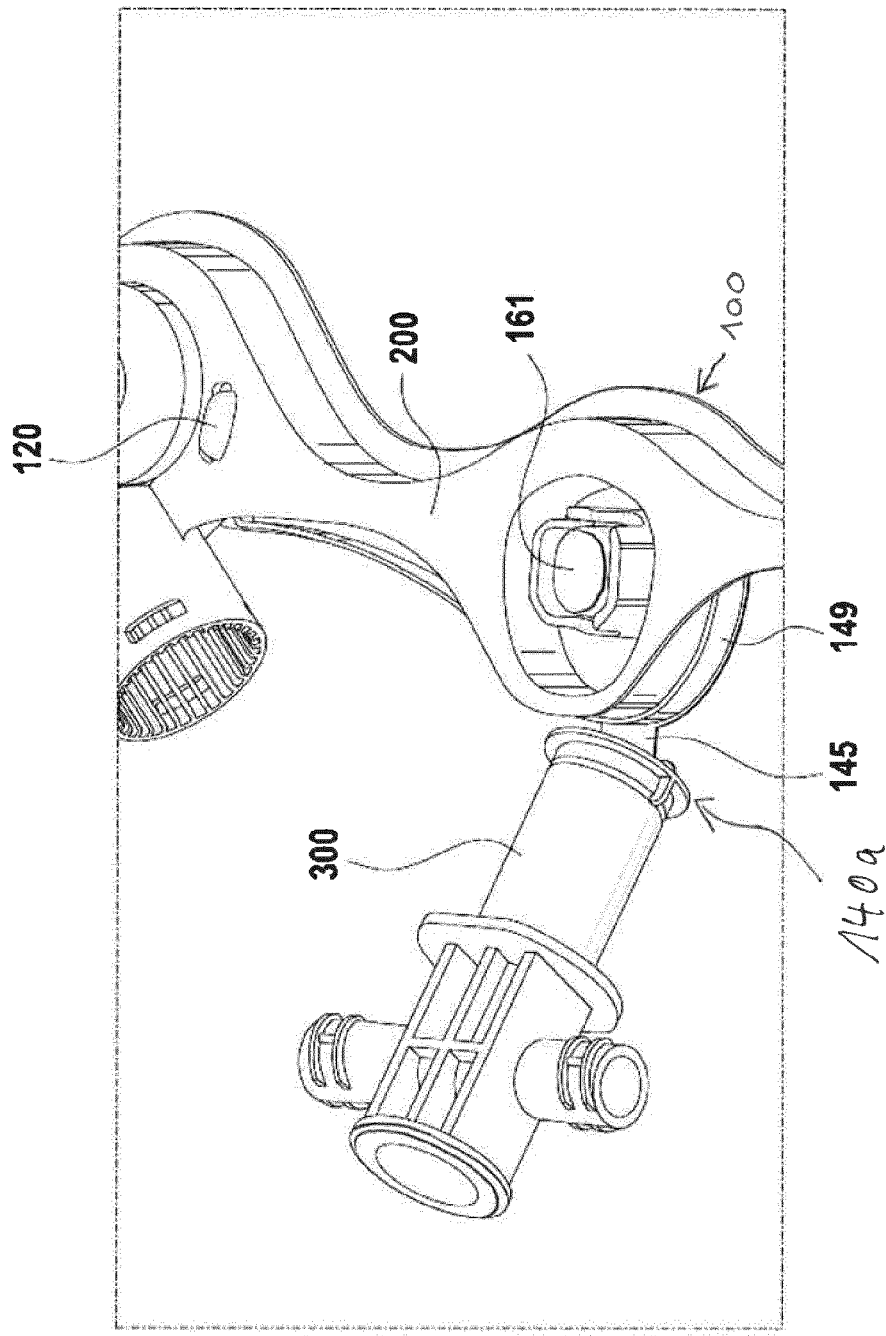
FIG. 11 shows the contact protection apparatus of FIGS. 9 and 10, being connected with the hard part of the cassette.

As an example for tubes which can be held by the fixing device 140, tubes are mentioned herein which in their use are connected at least once by a rinse port adapter 300 to a rinse 5 port of the fluid treatment apparatus, which is shown in FIG. 8 and FIG. 11.

The fixing device 140 is in the example of FIG. 7 designed as a holder for the rinse port adapter 300, with the latter being inserted into the first.

In FIG. 7, the fixing device 140 is connected to the main body of the contact protection apparatus 100 by (here optionally) two film joints 141, 143. The film joints 141, 143 lie at opposite ends of a spacer 145 which is stiffer when or if compared to the film joints 141, 143. The latter allow the fixing device 140 to be bent by 90° to a position which can be seen in FIG. 8. It is apparent that no more than one film joint 141 or 143 is required for this purpose. However, as the number of film joints increases, the flexibility and suppleness of the fixing device 140 increases.

In the example of FIG. 7, the film joints 141, 143 are provided as examples for joints. They are produced in injection molding together with the main body of the contact protection apparatus 100, with the known advantages. Embodiments with hinges that have not been injected are also contemplated.

The concrete design of the film joints 141, 143 allows further advantageously to access injection molds without slider.

The fixing device 140 comprises a cylindrical insert 147 (or plug-in section) which is surrounded by an annular structure 149. There is a gap between the cylindrical insert section 147 and the annular structure 149, in which gap the front end of the rinse port adapter 300 can be retained after or through being inserted or, if necessary, jammed therein.

FIG. 8 shows the contact protection apparatus 100 of FIG. 7. A rinse port adapter 300 is detachably attached on the fixing device.

Figure 9:
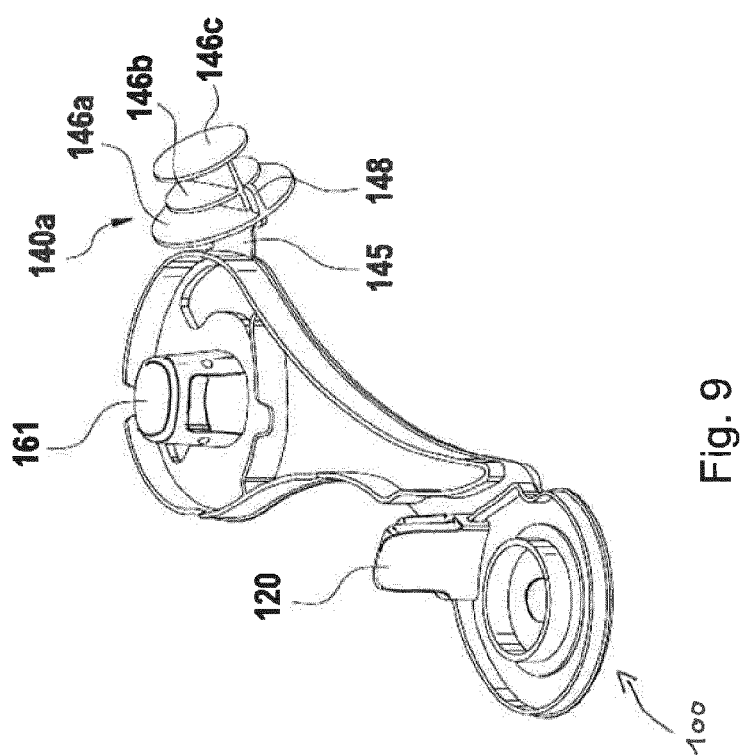
FIG. 9 shows the contact protection apparatus in perspective and from the bottom side in a third embodiment with a retaining or fixing device.

FIG. 9 shows the contact protection apparatus 100 in perspective and from the bottom side in a third embodiment with a retaining or fixing device 140a. Apart from the fixing device 140a, the contact protection apparatus 100 of FIG. 9 is not different from that of the preceding figures.

The embodiment of FIG. 9 may be injection-molded without a slide. Advantageously, there is also no need to core any undercut.

The embodiment of FIG. 9 permits a flexible connection between the fixing device 140a and the main body of the contact protection apparatus 100. A bending of the flexible holder by 45 degrees is shown in FIG. 9.

The fixing device 140a may optionally have three circular structures or surfaces 146a, 146b, 146c. For reasons of centering and better clamping, at least two of them are preferably provided for engagement in a cavity of the rinse port adapter 300.

One, two or more elastic arms 148 are optionally provided with the contact protection apparatus 100 in any embodiment, as exemplarily shown in FIG. 9. They may be provided to snap into the groove in the circumferential direction provided on the rinse port adapter 300.

Non-elastic clamping sections may also alternatively or additionally enable a detachable fixing of the rinse port adapter 300 on or at the fixing device 140a.

Both clamping sections and stop arms 148 may, as exemplarily shown in FIG. 9, be in a longitudinal direction of the rinse port adapter 300.

Figure 10:
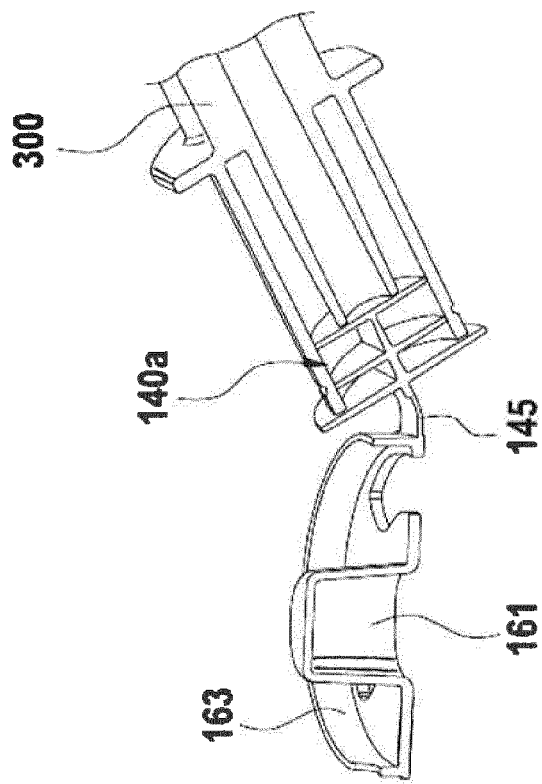
FIG. 10 shows the contact protection apparatus of FIG. 9 in a section, with slight perspective view on the cutting plane.

FIG. 10 shows the contact protection apparatus 100 of FIG. 9, cut through both the second connection section 160 and the retaining or fixing device 140a, with a slightly perspective view of the cutting plane.

FIG. 11 shows the contact protection apparatus 100 of FIGS. 9 and 10, connected to the hard part of the cassette 200. The rinse port adapter 300 is placed on the fixing device 140a.

The rinse port adapter 300 comprises two integral Luer connectors for the patient line. In this way, the retaining or fixing device 140a of the FIG. 11 may not only retain the patient lines, free of contamination, in the desired position on the cassette 200 using the contact protection apparatus 100, but also help do without the separate cover known from the state of the art for closing the rinse port adapter 300.

FIG. 12 shows a part of the contact protection apparatus 100 in perspective and from the bottom side in a fourth embodiment.

Unlike the preceding embodiments, the contact protection apparatus 100 comprises a drainage structure 170.

The drainage structure 170 exemplarily comprises, or consists of, grooves 171 which for example extend radially from the fixing device 140, not shown in FIG. 12, (see preceding figures), here the insert section 147.

In the example of FIG. 12, the grooves 171 extend on the bottom side between the raised insert section 147 and the annular structure 149, which surrounds the insert section 147.

The grooves 171 advantageously allow sterile steam or another sterilizing gas to reach various, if not all, surfaces of the rinse port adapter 300 during sterilization of the cassette 200, even if it is attached on the insert section 147.

LIST OF REFERENCE NUMERALS 100 contact protection apparatus
110 covering section
111 first structure
113 second structure
120 first connection section
121 spacer
130 encoding structure
140 fixing device
140a fixing device
141 film joint
143 film joint
145 spacer
146a circular surface
146b circular surface
146c circular surface
147 insert or plug-in section
148 elastic stop arm or pusher arm
149 annular structure
150 grip section
151 structure
151a recess
151b recess
160 second connection section
161 projection
161a protrusion
161b protrusion
163 structure
163a recess
163b recess
165 first through-opening
167 second through-opening
170 drainage structure
171 grooves
200 fluid-conducting cassette
241 connection point
241a channel structure
242 centering opening or retaining opening
251 bar
252 closed structure
253 connector
255 connector
261a nose
261b nose
261c nose
265 projection
267 projection
300 rinse port adapter

The invention claimed is:

1. A contact protection apparatus for covering a connection point of a medical fluid-conducting cassette for a medical fluid treatment, the contact protection apparatus comprising:
   a first side,
   a second side opposite the first side,
   at least one covering section for covering the connection point before use of the medical fluid-conducting cassette,
   a first connection section configured to detachably connect the contact protection apparatus to or hold the contact protection apparatus on the medical fluid-conducting cassette, the first connection section comprising an insert or plug-in connection or part thereof; and
   a second connection section configured to detachably connect the contact protection apparatus to or hold the contact protection apparatus on the medical fluid-conducting cassette, the second connection section comprising a projection configured to be inserted into a centering opening of the medical fluid-conducting cassette.

2. The contact protection apparatus according to claim 1, wherein the at least one covering section comprises a first structure projecting from the second side of the contact protection apparatus, wherein the first structure has a closed circumference.

3. The contact protection apparatus according to claim 2, wherein the at least one covering section comprises a second structure projecting from the second side of the contact protection apparatus, wherein the second structure has a closed circumference.

4. The contact protection apparatus according to claim 1, further comprising a grip section, wherein the grip section comprises a structure projecting from the second side of the contact protection apparatus, wherein the structure has a closed circumference.

5. The contact protection apparatus according to claim 4, wherein the structure of the grip section comprises at least one recess in an outer edge of the structure.

6. The contact protection apparatus according to claim 1, wherein the second connection section comprises a structure projecting from the second side of the contact protection apparatus, wherein the structure has a closed circumference.

7. The contact protection apparatus according to claim 6, wherein the structure of the second connection section comprises a recess in an outer edge of the structure.

8. The contact protection apparatus according to claim 1, wherein a grip section is arranged between the first connection section and the second connection section.

9. The contact protection apparatus according to claim 1, wherein the contact protection apparatus comprises a first through-opening in an area of the second connection section.

10. The contact protection apparatus according to claim 1, wherein the contact protection apparatus comprises a spacer in an area of the first connection section.

11. The contact protection apparatus according to claim 1 further comprising an encoding structure for an arrangement which is encoded on the medical fluid-conducting cassette according to a shape of the contact protection apparatus.

12. The contact protection apparatus according to claim 1, further comprising a fixing device for detachably receiving or retaining inlet and outlet tubes of the medical fluid-conducting cassette or for detachably receiving or retaining inlet or outlet tubes of the medical fluid-conducting cassette.

13. The contact protection apparatus according to claim 12, wherein the fixing device is arranged only on one side of the contact protection apparatus.

14. The contact protection apparatus according to claim 13, wherein the at least one covering section is separate from a grip section.

15. The contact protection apparatus according to claim 1, wherein the contact protection apparatus is produced unitarily as a one-piece apparatus.

16. A medical fluid-conducting cassette system, comprising:
a medical fluid-conducting cassette; and
a contact protection apparatus comprising:
a first side,
a second side opposite the first side,
at least one covering section for covering a connection point of the medical fluid-conducting cassette before use of the medical fluid-conducting cassette,
a first connection section configured to detachably connect the contact protection apparatus to or hold the contact protection apparatus on the medical fluid-conducting cassette, the first connection section comprising an insert or plug-in connection or part thereof, and
a second connection section configured to detachably connect the contact protection apparatus to or hold the contact protection apparatus on the medical fluid-conducting cassette, the second connection section comprising a projection configured to be inserted into a centering opening of the medical fluid-conducting cassette.

17. The medical fluid-conducting cassette system according to claim 16, wherein the contact protection apparatus is attached to the medical fluid-conducting cassette without any adhesives.

18. The medical fluid-conducting cassette system according to claim 16, wherein the contact protection apparatus comprises a section that protrudes from an edge of the medical fluid-conducting cassette.

19. The medical fluid-conducting cassette system according to claim 18, wherein a grip section of the contact protection apparatus is arranged on the section that protrudes from the edge of the medical fluid-conducting cassette.

20. The medical fluid-conducting cassette system according to claim 16, wherein the first connection section of the contact protection apparatus mechanically prevents the medical fluid-conducting cassette from being mounted to a blood treatment apparatus.

21. The medical fluid-conducting cassette system according to claim 16, wherein the first connection section of the contact protection apparatus connects the contact protection apparatus to a retaining opening or the centering opening of the medical fluid-conducting cassette for intake of the medical fluid-conducting cassette at a blood treatment apparatus.

22. The medical fluid-conducting cassette system according to claim 16, wherein the contact protection apparatus is configured to be sterilized with the medical fluid-conducting cassette.

23. The medical fluid-conducting cassette system according to claim 22, wherein the at least one covering section of the contact protection apparatus is manually detachable from the medical fluid-conducting cassette.

24. The medical fluid-conducting cassette system according to claim 22, wherein the at least one covering section of the contact protection apparatus is manually detachable from the connection point.

25. The medical fluid-conducting cassette system according to claim 16 further comprising:
an encoding structure on the medical fluid-conducting cassette that is shaped to correspond to a shape of the contact protection apparatus; and
an edge contour that corresponds to a contour of the encoding structure of the contact protection apparatus.

26. The medical fluid-conducting cassette system according to claim 16, wherein at least one connection point is a fluid fitting for a substituate line.

27. The medical fluid-conducting cassette system according to claim 16, wherein the medical fluid-conducting cassette is a blood cassette.

28. The medical fluid-conducting cassette system according to claim 16, wherein a depth of the centering opening of the medical fluid-conducting cassette is greater than a height of the projection of the second connection section.

29. The medical fluid-conducting cassette system according to claim 16, wherein an area of the second connection section comprises a plurality of projections, wherein geometries of the projections are adapted to a shape of a first through-opening and to a shape of a second through-opening.

30. The medical fluid-conducting cassette system according to claim 16, wherein an area of the second connection section comprises a plurality of projections, wherein geometries of the projections are adapted to a shape of a first through-opening or to a shape of a second through-opening.

\* \* \* \* \*